United States Patent
Puleo et al.

(10) Patent No.: US 9,199,201 B2
(45) Date of Patent: Dec. 1, 2015

(54) SELF CONTAINED ELECTROOSMOTIC PUMP AND METHOD OF MAKING THEREOF

(75) Inventors: Christopher Michael Puleo, Glenville, NY (US); Ralf Lenigk, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 528 days.

(21) Appl. No.: 13/429,471

(22) Filed: Mar. 26, 2012

(65) Prior Publication Data

US 2013/0156615 A1    Jun. 20, 2013

Related U.S. Application Data

(63) Continuation-in-part of application No. 13/326,653, filed on Dec. 15, 2011.

(51) Int. Cl.
| | |
|---|---|
| *F04B 35/04* | (2006.01) |
| *B23P 15/00* | (2006.01) |
| *B01D 61/42* | (2006.01) |
| *A61K 9/00* | (2006.01) |

(Continued)

(52) U.S. Cl.
CPC .......... *B01D 61/427* (2013.01); *A61K 9/0004* (2013.01); *F04B 17/00* (2013.01); *F04B 19/006* (2013.01); *A61M 2005/14204* (2013.01); *A61M 2005/14513* (2013.01)

(58) Field of Classification Search
CPC .............. A61K 9/0004; B01D 61/427; A61M 2005/14204; A61M 2005/14513; F04B 17/00; F04B 19/006

USPC .................... 417/48; 204/450, 451, 600, 601
See application file for complete search history.

(56) References Cited

U.S. PATENT DOCUMENTS

| | | |
|---|---|---|
| 4,673,483 A | 6/1987 | Mandle |
| 5,840,443 A | 11/1998 | Gregg et al. |

(Continued)

FOREIGN PATENT DOCUMENTS

GB     1452104 A    10/1976

OTHER PUBLICATIONS

Vajandar et al., "Electro-Osmotic Pumping and Ionic Conductance Measurements in Porous Membranes", Graduate School of Vanderbilt University, pp. 1-148, Dec. 2009.*

(Continued)

*Primary Examiner* — Peter J Bertheaud
*Assistant Examiner* — Dominick L Plakkoottam
(74) *Attorney, Agent, or Firm* — Eileen B. Gallagher

(57) ABSTRACT

A pump comprises a plurality of electroosmotic membranes comprising one or more positive electroosmotic membranes and one or more negative electroosmotic membranes; and a plurality of electrodes comprising one or more cathodes and one or more anodes. The electrodes are pre-charged, chargeable, rechargeable or combinations thereof and the cathode and anode are operatively coupled to each other. The positive electroosmotic membranes and negative electroosmotic membranes are disposed alternatively and at least one cathode is disposed on one side of one of the membranes and at least one anode is disposed on another side of that membrane, and wherein at least one cathode or anode is disposed between a positive electroosmotic membrane and a negative electroosmotic membrane. The pump is an electroosmotic pump.

27 Claims, 7 Drawing Sheets

(51) Int. Cl.
*F04B 17/00* (2006.01)
*F04B 19/00* (2006.01)
*A61M 5/142* (2006.01)
*A61M 5/145* (2006.01)

(56) References Cited

U.S. PATENT DOCUMENTS

| | | | |
|---|---|---|---|
| 7,235,164 B2* | 6/2007 | Anex et al. | 204/600 |
| 7,267,753 B2 | 9/2007 | Anex et al. | |
| 7,316,543 B2* | 1/2008 | Goodson et al. | 417/50 |
| 7,540,717 B2 | 6/2009 | Sheng et al. | |
| 7,629,133 B2 | 12/2009 | Schlenoff | |
| 7,727,363 B2 | 6/2010 | Jacobson et al. | |
| 7,976,535 B2 | 7/2011 | Ehwald et al. | |
| 8,057,191 B2 | 11/2011 | Khamizov et al. | |
| 2003/0075445 A1* | 4/2003 | Woudenberg et al. | 204/451 |
| 2003/0085024 A1 | 5/2003 | Santiago et al. | |
| 2004/0182707 A1* | 9/2004 | Jardemark et al. | 204/451 |
| 2006/0094945 A1* | 5/2006 | Barman et al. | 600/347 |
| 2006/0108286 A1* | 5/2006 | Hambitzer et al. | 210/637 |
| 2007/0175768 A1 | 8/2007 | Lau et al. | |
| 2008/0210559 A1 | 9/2008 | Chen et al. | |
| 2010/0038245 A1* | 2/2010 | Small et al. | 204/520 |
| 2010/0147689 A1 | 6/2010 | Chen et al. | |
| 2011/0052431 A1 | 3/2011 | Heldal et al. | |
| 2013/0041353 A1* | 2/2013 | Shin et al. | 604/892.1 |

OTHER PUBLICATIONS

Tzu-Chi Kuo et al., "Manipulating Molecular Transport through Nanoporous Membranes by Control of Electrokinetic Flow: Effect of Surface Charge Density and Debye Length", ACS Publications, vol. 2001, Issue No. 20, pp. 6298-6303, Sep. 8, 2001.

Graeme A. Snook et al.; "Conducting-polymer-based supercapacitor devices and electrodes"; Journal of Power Sources 196 (2011) 1-12; Corresponding author. Tel.: +61 3 95458863; fax: +61 3 95628919. E-mail address: Graeme.Snook@csiro.au (G.A. Snook).

Hyun-Ho Yang et al. "Modeling, fabrication and demonstration of an electrostatic actuator with a coplanar pre-charged electrode"; Recieved Nov. 8, 2010, in final form May 26, 2011, Published Jun. 30, 2011, Online at stacks.iop.org/JMM/21/085012; 10 pages.

Search Report and Written Opinion from corresponding PCT Application No. PCT/EP2012/075469 dated Apr. 15, 2013.

\* cited by examiner

SELF CONTAINED ELECTROOSMOTIC PUMP AND METHOD OF MAKING THEREOF

CROSS REFERENCE TO RELATED APPLICATIONS

This application is a continuation-in-part of U.S. patent application Ser. No. 13/326,653, entitled "Electroosmotic pump and method of use thereof", filed Dec. 15, 2011; which is herein incorporated by reference.

STATEMENT REGARDING FEDERALLY SPONSORED RESEARCH & DEVELOPMENT

This invention was made with Government support under contract number HDTRA1-10-C-0033 awarded by the Defense Threat Reduction Agency. The Government has certain rights in the invention.

FIELD

The invention relates to a non-mechanical pump, and more particularly to an electroosmotic pump (EOP) that generates high pressure using a comparatively lower voltage and is independent of an external power source, and is further associated with methods of making the EOP.

BACKGROUND

Pumps can be classified into mechanical and non-mechanical varieties. Generally, the conventional mechanical pumps have issues with reliability of the moving pump-components. Electrokinetic pumps, on the other hand, contain no moving parts, making them suitable for a variety of applications, including fluid movement in microanalytical systems. EOPs are electrokinetic pumps, and provide a fluid flow due to movement of an electric double layer that forms at the solid-liquid interface. Application of an electric field across a porous membrane structure of an EOP results in a movement of the electric double layer, which results in a viscous drag. The viscous drag then causes a bulk fluid flow and generation of a net pressure.

Standard EOPs made from porous ceramic frit or packed capillaries require over 1 kV to establish the electric fields required for pumping. The electric field is generated using at least two electrodes disposed on either side of the porous membrane and an external power source. Generally, the current from the electrode is passed into the pumping solution via chemical reactions at the electrode surface, e.g. using a Pt electrode and water as the pumping solution to produce gases like hydrogen or oxygen, which may stall the pump. Alternative electrode materials are used in electrokinetic pumps, such as redox polymers, redox metal salts or oxides.

In addition to the alternative electrode materials, thin porous ceramic substrates have recently been employed to produce the highest pumping pressure per applied voltage due to high surface-to-volume ratios. The EOP for generating high pressure using low-voltage, external power source and thin EOP substrates, is recently being developed. In general, to increase the pumping pressure of low-voltage EOPs, increased surface area for electric double layer formation is required, however, increasing the thickness of the EOP substrate results in higher running voltages.

The alternate stacking arrangement of electrodes and membranes for a high pressure EOP solved the challenge of maintaining high electric field strengths using low running voltages. However, the need for self-containment of pumps and actuators in analytical, biomedical, pharmaceutical, environmental, and security monitoring applications has not been met. Therefore, the EOPs which are capable of generating high pressure using a lower applied voltage, without using an external power source, and with minimum membrane fabrication requirements, are desirable.

BRIEF DESCRIPTION

The EOPs, as described herein, that comprises a plurality of membranes and pre-charged or chargeable electrodes solve the above mentioned problems by eliminating the need for external power sources to drive EOPs and generating a high pressure every at a lower applied voltage. The use of self-contained high pressure EOPs further reduce the expense and spatial requirements for implementing EOP based fluid control in larger systems and devices.

One example of a pump, comprises a plurality of electroosmotic membranes comprising one or more positive electroosmotic membranes and one or more negative electroosmotic membranes; and a plurality of electrodes comprising one or more cathodes and one or more anodes; wherein the electrodes are pre-charged, chargeable, rechargeable or combinations thereof and the cathode and anode are operatively coupled to each other, wherein the positive electroosmotic membranes and negative electroosmotic membranes are disposed alternatively, wherein at least one cathode is disposed on one side of one of the membranes and at least one anode is disposed on another side of that membrane, and wherein at least one cathode or anode is disposed between a positive electroosmotic membrane and a negative electroosmotic membrane.

An example of pump of the invention, comprises a plurality of electroosmotic membranes comprising one or more positive electroosmotic membranes and one or more negative electroosmotic membranes, wherein each of the positive electroosmotic membranes and negative electroosmotic membranes are disposed alternatively; a plurality of electrodes comprising one or more cathodes and one or more anodes, wherein the electrodes are pre-charged, chargeable, rechargeable or combinations thereof and the cathode and anode are operatively coupled to each other, wherein at least one cathode is disposed on one side of one of the membranes and at least one anode is disposed on another side of that membrane, wherein at least one of the cathodes or anodes is disposed between a positive electroosmotic membrane and negative electroosmotic membrane, and wherein the electrodes are operatively coupled to generate and store a voltage up to 3 volts to generate a pressure of at least about 0.75 PSI.

An example of a method of making a pump of the invention, comprises disposing a plurality of membranes, comprising one or more positive electroosmotic membranes and one or more negative electroosmotic membranes, in an alternative fashion to form a membrane stack, disposing a plurality of electrodes comprising cathodes and anodes, wherein the electrodes are pre-charged, chargeable, rechargeable or combinations thereof and wherein at least one of the cathodes is disposed on one side of one of the positive electroosmotic membrane or negative electroosmotic membranes and at least one of the anodes is disposed on another side of that membrane, and at least one of the cathodes or anodes is disposed between a positive electroosmotic membrane and negative electroosmotic membrane, and operatively coupling the electrodes to complete a circuit for activating the electrodes to generate a chemical potential across the membranes.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
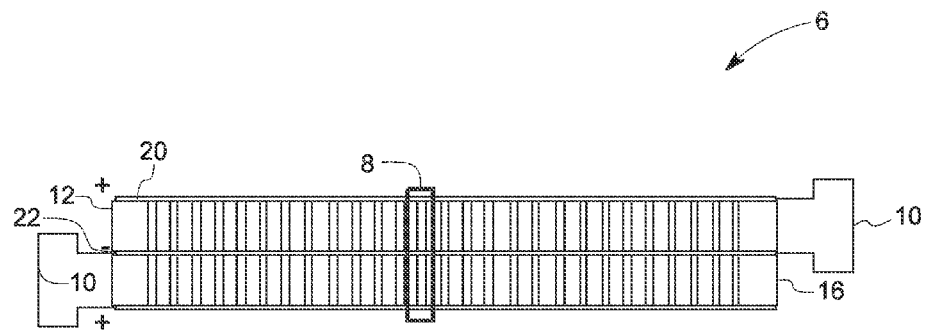
FIG. 1 is a schematic drawing of an example of a self-contained unit EOP comprising at least two electroosmotic membranes and three pre-charged electrodes.

One or more of the embodiments of the invention relate to a pump comprising a plurality of electrodes and electroosmotic membranes, wherein the pump is capable of operating independent of an external power source. Therefore, the pump is a self-contained system, wherein self-containment refers to the elimination of power, pressure, and input sources external to the device. In one or more examples, the pump is an EOP that generates high pressure sing lower applied voltage without using any external power source. The EOPs solve the problem of self-contained fluidic systems in part by using electrodes, which are pre-charged, chargeable, rechargeable or combinations thereof.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

As used herein, the term "electroosmotic membranes" refers to the membranes which are capable of maintaining electroosmotic flow of a fluid using electroosmosis. Electroosmosis is a motion of a fluid containing charged species relative to a stationary charged medium by applying an external electric field. Electroosmotic flows are useful in microfluidic systems because the flow enables fluid pumping and control of the flow-rate without using mechanical pumps or valves.

As used herein, the term "positive electroosmotic membrane" refers to a porous membrane with surface properties, such that induced electroosmotic flow occurs in the direction of the applied electric field deionized water. The magnitude and direction of electroosmotic flow is dependent on the operating parameters, including the type or running liquid or buffer system used.

As used herein, the term "negative electroosmotic membrane" refers to a porous membrane with surface properties, such that induced electroosmotic flow occurs in the direction opposing the applied electric field in deionized water. The magnitude and direction of electroosmotic flow is dependent on the operating parameters, including the type or running liquid or buffer system used.

As used herein, the term "porous material" refers to a material with a plurality of pores, wherein the material is macroporous, microporous, or nanoporous. The porous material may form "porous membranes" and "porous electrodes". The pore can be macropores, micropores or nanopores. In the case of micropores, the average pore size may be, for example, less than about 10 microns, or less than about 5 microns, or less than about one micron. In case of nanopores, the average pore size may be, for example, about 20 nm to about 800 nm, or about 20 nm to about 500 nm, or about 10 nm to about 300 nm. The porous membranes may be made of inorganic materials such as, silicon, alumina, silicon nitride, or silicon dioxide. The porous electrodes may be made of redox materials, such as metal salts or conductive polymers.

As used herein, the term "interspersed" or "intervening" refers to a position of a membrane or an electrode which is present between two other electrodes or two other membranes respectively. For example, a membrane that is interspersed means the membrane is disposed between two different electrodes, wherein the electrodes are oppositely charged. In another example, an electrode that is intervened or interspersed means the electrode is disposed between two membranes with opposite surface charges. The term "disposed between" is alternatively used herein as "interspersed" or "intervened".

As used herein, the term "battery-free EOP" refers to an EOP with no external power source or battery. The EOP has an integrated power source in the electrodes of the EOP, which drives the EOP function and generates high pressure. In one embodiment, the "battery-free EOP" has pre-charged or chargeable or re-chargeable electrodes which are able to store chemical charges for some time and supply the power for the EOP operation.

As used herein, the term "pre-charged" refers to an electrode which is induced with charges and able to store that charge for EOP operation and are ready to be used for the pumping operation. In some embodiments, the EOP comprises pre-charged electrodes during assembly or packaging of the EOP, so that the EOP is ready to use without charging the electrodes. As used herein, the term "chargeable electrode" refers to an electrode which is charged up before operating the EOP. The chargeable electrodes are devoid of pre-induced charges during assembly or packaging of the EOP and induced with charges at any point of time before operating the EOP. As used herein, the term "re-chargeable electrode" refers to an electrode which has the ability to be induced with charges repeatedly and drives the electrode operation for pumping fluids. The chargeable or re-chargeable electrodes may also be packaged with the EOP.

Various embodiments of the pumps comprise a plurality of electroosmotic membranes and a plurality of electrodes comprising cathodes and anodes, wherein the electrodes are pre-charged, chargeable, rechargeable or combinations thereof. The oppositely charged electrodes, such as cathodes and anodes are operatively coupled to each other. The electroosmotic membranes comprise one or more positive electroosmotic membranes and one or more negative electroosmotic membranes, which are disposed alternatively. At least one cathode is disposed on one side of one of the membranes and at least one anode is disposed on another side of that membrane, and wherein at least one cathode or anode is disposed between a positive electroosmotic membrane and a negative electroosmotic membrane. In one or more embodiments, the pumps are EOPs. The EOP drives fluid flow independent of an external power supply.

As noted, the cathodes and anodes are coupled to each other, for example, by a wired connection, at the time of operating the EOP. In one or more embodiments, when the two electrodes are coupled by a metal wire, an electron is allowed to flow through the metal wire for each positive ion passed in the fluid of the EOP. The ionic flow through the membrane results an electroosmotic flow that generates a chemical potential across the membrane. The positive ion is passed through the nanopores of the membrane, which drives the ionic fluid to flow through the EOP and generates a pressure. The EOP is configured to generate high pressure compared to conventional EOPs using a low voltage. In one or more embodiments, the EOP is configured to generate a pressure of at least about 0.75 PSI.

In one or more embodiments, the "battery-free EOP" may pump liquid through the membranes using the stored chemical potential in the electrodes, when the electric circuit is closed. Accordingly, the electrodes are coupled to each other, for example, by a wired connection to allow the electron flow through the closed circuit, which results in a flow of ions generated in the fluid of the EOP through the membranes. The electron flow typically results in a discharge of the chemical potential stored in the electrodes that drives the fluid-flow which further enables the pumping mechanism.

Once the circuit is opened, the fluid movement discontinues due to the termination of the electron flow. The termination of the electron flow in the open circuit subsequently hinders the discharge of the chemical potential that drives the fluid-flow. Reconnecting the electrodes to close the circuit causes the fluid to start flowing again as a result of the discharge of the chemical potential energy that is stored in the electrodes. Hence, the closed circuit enables continuous "battery free" EOP operation.

In one embodiment, a simplified structure of the EOP, which is alternatively referred to herein as "unit structure of EOP" or "unit of EOP", comprises at least two electroosmotic membranes and at least three pre-charged electrodes, wherein the electroosmotic membranes comprise one positive electroosmotic membrane and one negative electroosmotic membrane and the pre-charged electrodes comprise at least two cathodes and one anode or at least two anodes and one cathode. A unit EOP structure 6 is illustrated in FIG. 1. The unit EOP is independent of an external power source, as in some embodiments, the electrodes are previously induced with the electric charges as pre-charged electrodes. In other embodiments, the electrodes may also be chargeable before use of the EOP. Both of the pre-charged or chargeable electrodes may be rechargeable.

As noted, for chargeable, rechargeable or pre-charged electrodes, the electrodes may be separately charged and then may be assembled in an EOP. In some embodiments, the electrodes present in an EOP are charged before use. In some embodiments, while charging the electrodes for storage, at least one membrane is interspersed between the two oppositely charged electrodes. The charged electrodes may then be assembled with multiple membranes to build a "battery free" EOP. For a battery free EOP, two charged electrodes are sufficient for pumping fluid, although additional electrodes may be used. In some embodiments, the charge is stored in three electrodes, which may further be utilized by using a unit of EOP, comprising at least two membranes and at least three electrodes. In some embodiments, multiple charged electrodes may be assembled with multiple membranes to form an integrated EOP comprising more than one unit EOP.

Figure 2:
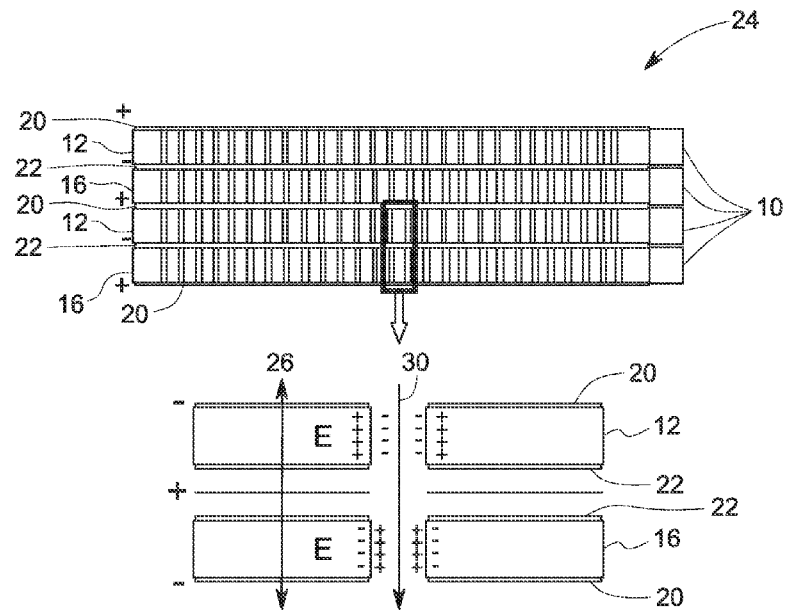
FIG. 2 is a schematic drawing of an example of an EOP with multiple pre-charged electrodes and multiple membranes having alternating (+/−) surface charge.

The plurality of porous electroosmotic membranes and electrodes are fabricated in a layer-by-layer configuration, wherein the alternatively charged membranes are stacked one after another, as shown in FIG. 2. In some embodiments, the electrodes are disposed on both sides of each of the membranes forming intervening layers between the stacked membranes. For example, a pre-charged electrode is disposed on the surface of a porous membrane, wherein the porous membrane is AAO or cellulose.

In one embodiment, a cathode is disposed on a negative electroosmotic membrane and an anode is disposed on the other side of the negative electroosmotic membrane, which results in the negative electroosmotic membrane to intersperse between the cathode and anode. In another embodiment, an anode is disposed on (upstream of) a positive electroosmotic membrane and a cathode is disposed on other side (downstream) of the positive electroosmotic membrane, such that the positive electroosmotic membrane is interspersed between the anode and cathode.

Various arrangements or rearrangements of the membranes and electrodes are possible, while maintaining alternatively charged membranes stacked with two oppositely charged electrodes on both sides of each of the membranes and keeping one electrode common between each of the two membranes. In one embodiment, only one of the cathodes or anodes is disposed between two oppositely charged electroosmotic membranes. For example, the unit structure of EOP have one anode which is common between a positive electroosmotic membrane and negative electroosmotic membrane, and results in a sequential disposition of a cathode, a positive electroosmotic membrane, an anode, a negative electroosmotic membrane, and then again another cathode. In another exemplary configuration, the unit EOP structure has one cathode which is common between the positive electroosmotic membrane and negative electroosmotic membrane, which results in a sequential disposition of an anode, a positive electroosmotic membrane, a cathode, a negative electroosmotic membrane, and then again, another anode.

As noted, in some exemplary embodiments, multiple units of EOPs are stacked together, wherein the multiple electroosmotic membranes and electrodes are arranged in alternative layers. Each of these layers remains electrically insulated due to the alternating anode/cathode arrangement, without physical insulation of the electrode material itself. In one example, a first unit of an EOP is followed by a second unit of an EOP, wherein the second unit of the EOP comprises a negative electroosmotic membrane that is disposed either upstream or downstream of the positive electroosmotic membrane of the first unit of the EOP. For example, in one embodiment, the negative electroosmotic membrane of the second unit of the EOP is disposed downstream of an anode of the first unit of the EOP, and a cathode is disposed on the directionally opposite side of the negative electroosmotic membrane, such that the membrane is interspersed between the anode and cathode. The interspersed negative electroosmotic membrane is further followed by a positive electroosmotic membrane, which is disposed downstream of the cathode, and an anode is further disposed on the directionally opposite side of the positive electroosmotic membrane to form the second unit of the EOP that is situated downstream of the first unit of the EOP. In some other embodiments, a third unit of an EOP is further formed downstream of the second unit of the EOP, a fourth unit of an EOP is further formed downstream of the third unit of the EOP, and so on. Hence, by stacking the multiple units of the EOPs, a single "integrated EOP" is generated, wherein the integrated EOP comprises multiple membranes and electrodes and the electrodes are present as intervening layers between each of the membranes.

The multiple units of the EOPs provide increasing pump surface area to the single integrated EOP, which generates higher pumping pressure without using complicated fabrication or higher input voltage. The stacking architecture thus enables high pressure pumping at low voltages, resembling a single unit of an EOP. Multiple low-voltage, high pressure EOPs may be used together in a series or in parallel.

An electrical double layer is formed in each alternating layer of the EOP and moves in the same direction through the membrane stack due to the alternating positive and negative electroosmotic membrane. Depending on the ionic concentration, the thickness of the electric double layer, which is referred to as the Debye length, varies from 3 nm to 300 nm for deionized water. The Debye length may become comparable to the nanopores within the EOP, depending on the electroosmotic membrane used. Furthermore, the use of thin membranes and corresponding interspersed electrodes enables the application of high electric field strengths across each of the alternating electroosmotic membranes. To increase pumping pressure, a larger surface area is required for double layer formation, without affecting field strength across the pores. In the EOP stack, the oppositely charged Debye layers move through the successive electric fields, and the net movement results in relatively higher electroosmotic pressure development due to the dense arrangement of the pores.

Polarity of the surface and zeta potential dictates the electroosmotic flow direction. The basic flow principle of EOPs is based on the surface charge of the membranes and the formation of electrical double layers. For example, when an aqueous solution contacts a glass surface for silica), the glass surface becomes negative due to the deprotonation of surface silanol groups. An electrical double layer forms at the surface as a result of the deprotonation. The surface charge attracts dissolved counter-ions and repels co-ions, resulting in a charge-separation and forming an electrical double layer. The mobile ions in the diffused counter-ion layer are driven by an externally applied electrical field. The moving ions drag along the bulk liquid through the membranes and develop the electroosmotic flow. The EOP stack enables formation of a large surface area for electric double layer, without increasing the overall diameter of the pores or the electric field strength across each individual pore. Thus, higher pumping pressure is obtained without necessitating high driving voltage.

Unlike conventional pumps, one or more embodiments of the EOP generate high pressure at comparatively lower applied voltages, without the need for an external power source. The electroosmotic flow of the fluid builds up an electroosmotic pressure in the EOP using the potential energy stored in the electrodes. The pumping pressure may be tuned or modified based on the requirement of various applications, in some embodiments, the EOP is configured to generate a pressure of at least about 0.5 PSI. Unlike conventional single membrane EOPs which generate pressure between 0.1 and 0.75 PSI, multiple membrane-stacked EOP generates more pressure, in some embodiments, about 1 PSI. In one or more embodiments, using different membranes, such as anodic aluminum oxide (AAO) membrane, the pressure generated is at least about 0.75 PSI. In one embodiment, the EOP may generate a pressure of at least about 10 PSI, in another embodiment, the EOP may generate a pressure of about 100 PSI.

The amount of stored potential energy within the electrodes may be varied, however the capacity for storing potential energy is limited and depends on the redox potentials of the electrode materials used. In an exemplary embodiment, the EOP is configured to operate by applying at least 3 V potential across each of the membranes to achieve electric fields greater than 100 V/meter within the pump. In one example, the EOP is operated at 10 volts, in some other examples, the EOP is operated at less than or equal to 25 volts. As noted, the chemical potential for driving the EOP resides directly in the pump assembly, wherein the electrodes may be in a pre-charged, chargeable or rechargeable form.

One or more embodiments use pre-charged electrodes. In some embodiments, the pre-charged electrodes is used by chemically reducing/oxidizing a redox material prior to pump assembly. The pre-charged electrodes may be induced with charges before EOP operation, and after induced with charges, the electrodes are ready to be used upon application of pumping the fluids. In one or more embodiments, the electrodes comprise a material that generates a chemical potential of up to 3 V across the membranes. In one or more embodiments, the electrodes comprise a material capable of discharge slowly, for example, in a duration of 1 hour while running the pump with a flow rate between 0 and 10 µL/min/mm$^2$. In some embodiments, the electrodes discharge in a duration of 1 hour while running the pump with a flow rate between 0 and 5 µL/min/mm$^2$.

In some other embodiments, the electrodes may be devoid of pre-induced charges, however, the electrodes are configured to be induced with charges before operation. Accordingly, the chargeable electrodes may be induced with charges at any point of time before operating the EOP, through either chemical or electrochemical procedures, such as, soaking with an oxidizing or reducing agent or directly injecting electric current using an external power source. In one embodiment, the chargeable electrodes are packaged in an EOP, wherein the electrodes are not pre-induced with charges, however may be induced with charges before use.

In one or more embodiments, the electrodes are rechargeable, wherein the electrodes are repeatedly chargeable. In some embodiments, the electrodes are rechargeable for up to 5000 times. For each of the rechargeable electrodes, the electrode has a life time. The rechargeable electrodes may prevent unwanted side reactions to increase the cycle lifetime. The life time of a rechargeable electrode means the ability of the electrode to be charged up for pumping fluids for a number of times, for example, may be for 5 times or 10 times, and after that the electrodes may not be chargeable.

In one or more embodiments, the pre-charged or chargeable or re-chargeable electrodes are made of conducting polymers. Typical conducting polymers include polythiophenes, polypyrroles and polyanilines. The conducting polymers may have discharge capacities of about 100 mAh/g. The performance of the conducting polymers may be enhanced by the addition of nano-materials, such as carbon nanotubes. The discharge capacity may be increased by functionalizing the polymer with electroactive moieties. The conducting polymers may undergo fast redox reactions and consequently are capable of storing charge in the bulk material. Therefore, the conducting polymers are capable of performing redox reactions, and thereby the polymers may be referred to as redox polymer or pseudo-capacitors.

In one or more embodiments, the conducting polymer is an oxidation-reduction polymer material, metal oxide, graphene, or carbon nanotubes. In one embodiment, electrodes comprise a oxidation-reduction polymer or a redox polymer. The redox polymer or pseudo-capacitive materials may have advantages over carbon based super-capacitors in fast response time and superior specific energies, for example, the redox polymer may store a greater amount of energy per unit mass. The redox polymers may be more conductive than inorganic materials used in the batteries and consequently may have greater power generating capabilities. The redox conducting polymer or redox polymer, which has high conductivity, specific discharge capacity of greater than 200 mAh/g and a wide potential range with fast redox kinetics, are desirable for using as electrode material.

The redox polymers typically comprise spatially and electronically localized redox sites, unlike other conducting polymers. The redox sites are either covalently or electrostatically bound to the polymers. Two redox reactions may occur at the same potential at two different redox sites in redox polymers. Upon oxidation or reduction, the redox active molecule changes oxidation state without forming or disrupting any covalent bond, which minimizes the side reactions. The unwanted side reactions limit the charge storage of the electrodes, which affects the cycle lifetime of each of the pre-charged electrodes. The redox active molecules present in the electrode material undergo multiple cycles of oxidation/reduction reactions by conserving the overall charge and reducing the unnecessary side reactions.

In one or more embodiments, the redox polymer electrodes of the UN) are configured to maintain a long cycle lifetime. The redox polymers comprise a variety of materials, which cover a range of electrochemical potentials that results in a high voltage, however, the voltage may be selected in a range where the electrodes may not react irreversibly with solvents and electrolytes. Redox reactions generate redox complexes which are very stable having rapid electron transfer kinetics, and do not alter any chemical bonds during the electron transfer process. Therefore, the redox polymer electrodes may be discharged and recharged repeatedly without polymer degradation or polymer cracking. The electrochemical reversibility and the long-term integrity of the electrodes determine the utility and cycle lifetime of the electrodes for the battery free-EOP.

The composite electrodes of polymers with other materials may extend the cycle life time, improve conductivity, specific energy, and stability. Methods for improving cycle lifetime of conducting polymers are often limited by the swelling and consequent breakage of the polymer, and the method may include compositing with other materials, for example, carbon. In one or more embodiments, the electrode materials, such as redox polymers may form composites with other materials.

In some embodiments, the pre-charged electrodes include cathodes and anodes. One or more examples of the anode comprise an anode-active material, wherein the anode active material comprises a redox polymer charged to its reduced state. The anode may be employed in combination with various compatible electrolytes and cathodes in the EOP. The discharging mechanism in the electrodes involves electrochemical reactions at the redox polymer anode wherein the oxidation state of the anode changes to a higher oxidation state. For example, one of these electrodes may function as an anode when it is reduced from oxidation state (II) to the oxidation state (I) of a metal.

One or more examples of cathode include a cathode-active material, wherein the cathode-active material is a redox polymer in its oxidized state. The cathode may be employed with various compatible electrolytes and anodes in the EOP. The discharging mechanism in electrodes involves the electrochemical uncharging of the redox polymer cathode to a lower oxidation state. For example, an electrode functions as cathode when it is oxidized from the oxidation state (II) to the oxidation state (in) of the same metal or different.

In some embodiments, both the anode and cathode of the EOP comprise redox polymers. In one embodiment, the same redox polymer may be used for both the anode and cathode, in which case the redox polymer is oxidized on the cathode and reduced on the anode when the EOP is in its charged state. The redox polymer regains the same oxidation state on both the anode and cathode by discharging the electrodes. Starting from the discharged state, an electrode may be charged in either polarity, that is, either electrode may be employed as the anode. In an alternate embodiment, one redox polymer may be used for the anode and a different redox polymer may be used for the cathode. The method of chemically oxidized or reduced (p- or n-doped) polymer electrode before pump assembly thus eliminates the need for charging the polymers with an external voltage, which greatly enhanced the pump manufacturability.

In one or more embodiments, the electrode materials are macroporous, which allow transverse fluid flow. In some embodiments, the diameter of the macropores present on the electrodes may be in a range of 50 nm to 10 mm. In one embodiment, the diameter of the macropores is 1 mm. As noted, the electrodes are made of macroporous polymers, in some embodiments, the macroporous polymers may comprise glass or rubbery polymers, which maintain porosity in a dry state or when immersed in a solvent, may be used as electrodes. The macroporous polymers may include, but are not limited to, natural papers such as cellulose; synthetic paper such as polypropylenes or polyethylene, synthetic sponges such as polyethers, polyvinyl alcohol (PVA), or polyesters; or polymer mesh material such as polyurethane, polytetrafluoroethylene (PTFE), nylon, or polyethylene. In one embodiment, cellulose is used as electrodes, by soaking a paper in a conductive polymer.

In one or more embodiments, the redox polymers may include, but are not limited to poly(3,4-ethylenedioxythiophene) (Pedot):polystyrenesulfonate (PSS), Pedot-(molybdenum trioxide) $MoO_3$, poly(3-(4-fluorophenyl) thiophene) (MPFT), poly(3-(4-fluorophenyl)-thiophene) (PFPT), poly(3-methyl thiophene) (PMeT) or poly(1-cyano-2-(2-(3,4-ethylenedioxylthienyl)-1-(2-thienyl)vinylene (Th-CNVEDT) polymer. In some other embodiments, the electrode material may comprise pyridyl or polypyridyl complexes of transition metals like iron, ruthenium, osmium, chromium, tungsten and nickel. In some examples, the redox polymers be selected from trisvinylbipyridine or bisbipyridine dichloride derivative of metal, orphyrins (either free base or metallo derivatives), phthalocyanines (either free base or metallo derivatives), metal complexes of cyclams, such as tetraazacyclotetradecane, metal complexes of crown ethers, metallocenes such as ferrocene, cobaltocene and ruthenocene. In one embodiment, the redox polymer is Pedot:PSS. The Pedot has good compatibility with polar group polymers while doped with polyanion such as PSS. In organic media, the Pedot:PSS material may have lesser tendency to swell, which may indicate a high ionic resistance and a slow electrochemical processability. The ionic conductivity of Pedot may be improved by blending with an ionic conductor, such as polyethyleneoxide (PEO).

In one or more embodiments, the polymeric material used, as structural support for the electrodes, or as coating for the electrodes, is selected from poly(olefins), halogenated poly(olefins), poly(cylco olefins), halogenated poly(cylco olefins), poly(styrenes), halogenated poly(styrenes), poly(propylenes), poly(ethylenes), halogenated poly(ethylenes), poly(tetrafluoroethylenes), polyacetylenes, polyphenylene vinylenes, polypyrroles, polythiophenes, polyanilines, polyphenylene sulfide or polyfluorenes poly(ether sulfones), poly(arylsulfones), poly(sulfones), poly(phenylene ether sulfones), poly(imides), poly(etherimides), poly(vinylidene fluorides), poly(esters), halogenated poly(esters), poly(ethylene terephthalates), poly(butylene terephthalates), poly(carbonates), poly(vinyl halides), poly(acrylics), poly(acrylates), halogenated poly(acrylates), poly(methacrylics), poly(methacrylates), poly(anhydrides), poly(acrylonitriles), poly(ethers), poly(arylene ether ketones), poly(phenylene sulfides), poly(arylene oxides), poly(siloxanes), cellulose acetates, cellulose nitrates, poly(amides), nylon, ceramics and combinations thereof.

In some embodiments, the electrodes are made of a base material, such as a macroporous polymer, and coated with a conductive material. In one embodiment, the electrodes are coated with a redox polymer or a redox metal salt. In some embodiments, the electrodes are coated with redox polymers, which include but are not limited to Pedot, Pedot:PSS, poly(1,5-diaminoanthraquinone), poly(2-2-dithiodianiline) (pDTDA). The electrode may be coated with a conductive or redox polymer on a thick porous substrate.

In some embodiments, the redox polymer films or polymer coating on a substrate may be used as electrodes. Accordingly, the redox polymer films may be disposed on a metal or a non-metal substrate, wherein the film functions as an electrode. The electrode efficiency of the redox polymer film depends upon the diffusion layer as well as the thickness of the film. In one or more embodiments, the deposition of a film onto an electrode surface is through a spin-coating or dip-coating technique with a solution containing the redox polymers. The redox polymer film may be stably attached to the substrate, so that the redox complex formed in the reaction does not leach into the electrolyte solution. In one or more embodiments, the redox polymer may be deposited onto a glassy carbon or platinum electrode by electropolymerization resulting in a thin film of the polymer coating that functions as electrode.

In one embodiment of the EOP, the membranes and redox polymer electrodes are filled with deionized (DI) water. The reduced and oxidized portions of the electrodes interact with each other through the DI water filled in the nanopores. As noted, when the two charged redox polymer electrodes are coupled by a metal wire, such as 10 in FIG. 1, and an electron is allowed to flow through the metal wire 10 for each positive ion forms in the fluid of the EOP and passed through the nanopores 8 of the membrane (FIG. 1). The ionic flow through the membrane results electroosmotic flow induced by the stored chemical potential.

The chemical potential in the electrodes is generated without any input from the batteries or external power supplies. The electrodes comprise a material that is capable of storing chemical potential in electrodes, wherein the chemical potential generates a fluid flow through the membrane. In some embodiments, the chemical potential generated across the membrane is measured at nearly 1 V, for a specific electrode configuration. In one or more embodiments, stored charge at that potential is enough to cause 0.05 and 5 $\mu t/min/mm^2$ electroosmotic flows through the membrane. The flow rate may be altered by varying the surface area of the pump, and thus, the number of nanopores within the EOP. In one or more embodiments, the electrodes are capable of discharging for about 1 hour, thus providing sustained electroosmotic flow with flow rates greater than or equal to $0.5\ \mu L/min/mm^2$. The membranes are configured to operate the pump by applying an electric field of at least 100V/m across each of the membranes.

The chemical potential may be stored in the electrodes in a state that is dry, semi-dry or wet state. In a wet state, the EOP and electrodes are packaged in the running liquid, and flow is initiated by contacting oxidized and reduced electrodes, thus allowing discharge. In a semi-dry or gel state the electrodes are kept wet or hydrated to increase stability of their redox state electrode. In a dry state, the electrodes are in redox state and the charge remains stable despite dehydration. Thus, electroosmotic flow of fluids may be initiated by either rehydrating the dried EOP unit comprising pre-charged electrodes, or closing the electrical circuit across the two pre-charged electrodes in a EOP packaged with its running liquid.

As noted, the chemical potential generates a fluid flow through the membrane, therefore, water or liquid, for example, in bio-assays, may flow through the EOPs without the need for control equipment. Each step within the assay may be programmed into the membrane itself, thus enabling a new fluidic control platform based on stored chemical potential, instead of active electrical or pneumatic controls. Various factors may be used to control and pre-program the complex fluidic manipulations to run the EOPs. The factors include, but are not limited to, the surface area of the EOPs, the magnitude of the stored charge, duration of the circuit to be closed to activate the pump, or electronic components such as resistors that may control the discharge rate of the pumps, and combinations thereof.

As noted, the EOP is structured, so that each of the membranes is present between a positively charged electrode and a negatively charged electrode, eliminating the need for a semipermeable separator commonly associated with the conventional redox electrodes. As mentioned, each of the membranes may be interspersed between the two oppositely charged electrodes, such as a cathode and an anode, and each EOP unit within the stack is electrically isolated from the next. The configuration of the EOP, where each EOP unit within the stack is electrically isolated from the next, enables dense stacking of the nanoporous electroosmotic membranes, without changing the electric field strength across individual pores. For example, each of the anodes is disposed on one side of the electroosmotic membrane and each of the cathodes is disposed on the other side of the membrane.

In one or more embodiments, the membranes are porous, for example, macroporous, microporous or nanoporous. In some embodiments, the membranes are nanoporous with at least a 5% void space, which increases the efficiency. The diameter of the pores is typically between 10 nm to 500 nm. While stacking the membranes one after another, the pores of various membranes may be aligned in a straight line to form a continuous straight vertical channel starting from the top layer to the bottom layer, allowing a fluid to pass through the channels. In some embodiments, the pores of the various membranes may not be aligned in a straight line through the stacked membranes to form a straight channel. In these embodiments, although the pores are not aligned in a straight line, the fluid can still pass through the non-linear channels formed across multiple membranes.

Flow direction for positive electroosmotic membranes is different than that of the negative electroosmotic membranes. When the surface charge of the membrane is positive, the fluid flow proceeds in the direction of the electric field, and when the surface charge is negative, the fluid flow proceeds in the direction opposite to the electric field. The membranes may be stacked without individual electrical insulation. Therefore, the membranes are merged, with a common electrode in between two membranes, and the fabrication technique resolves any potential problem of individual electrical insulation, and increases the pressure using multiple membranes. The additive pressure in series results from the membrane stacking. In one or more embodiments, the EOP comprises 2 to 100 membranes.

The selection of electroosmotic membranes is typically restricted to a thin membrane, because the thin-nanoporous membrane structure increases the electric field strength at a given applied voltage. Each of the membranes has a thickness of about 10 nm to 10 mm. In one exemplary embodiment, 60 μm thick bare or silica-coated AAO membranes are used in the EOP stack, wherein the interspersed electrodes comprise a thicker, porous paper substrate coated with a redox conductive polymer where Pedot is disposed on the membrane surfaces.

Figure 7:
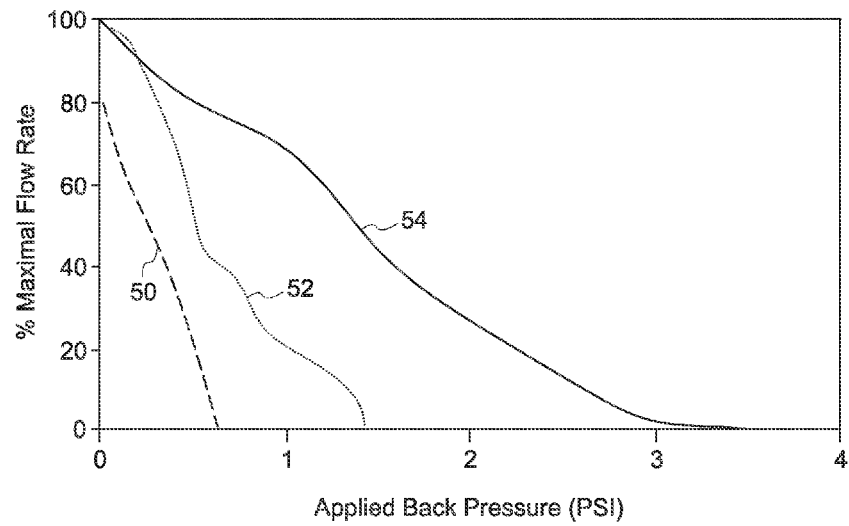
FIG. 7 is a graph showing increased pumping pressure of an EOP with multiple porous substrates.

The membrane structure, ° composition or number of membranes stacked in the EOP or combinations of two or more may affect the pumping pressure of an EOP. Conventional single membrane or single element EOPs provide pumping pressure between 0.1 and 0.75 PSI. In one or more embodiments, using different membranes, such as an AAO membrane, the pressure generated is at least about 0.75 PSI. In some embodiments, by increasing the number of electroosmotic membranes in an EOP for integrated EOP), the output pressure may be increased proportionally, as shown in FIG. 7. In one embodiment, the integrated EOP is configured to include multiple membranes stacked in a series to generate a pressure of at least about 10 PSI. In some other embodiments, the pressure is increased up to 100 PSI, by increasing the number of stacked membranes in an EOP. By stacking multiple units of EOPs to form an integrated EOP, which generates a high pressure independent of an external power source.

The composition of the electroosmotic membranes may vary. In some embodiments, the electroosmotic membranes comprise one or more dielectric materials or polymers with native grafted ionizable functionalities to achieve zeta potential similar to the dielectrics, and combinations thereof. The dielectric materials may comprise, but are not limited to, tungsten oxide, vanadium oxide, silicon dioxide or silica, common glasses such as silicates, silicon carbide, tantalum oxide, zirconium oxide, hafnium oxide, tin oxide, manganese oxide, titanium oxide, silicon nitride, chromium oxide, aluminum oxide or alumina, zinc oxide, nickel oxide, magnesium oxide and combinations thereof.

In some embodiments, the electroosmotic membrane may be an insulator. In some embodiments, the electroosmotic membrane may comprise an oxide, metal oxide or a metal nitride. Any of the oxides, metal oxides or nitrides may be used in the membrane, and may comprise, but are not limited to, hafnium oxide, zirconium oxide, alumina, or silica, as the insulators. The electroosmotic membranes may comprise polymers, selected from polydimethyl siloxane (PDMS), cyclic olefin copolymer (COC), polymethyl methacrylate (PMMA), poly carbonate (PC) or other materials with graftable surface chemistries.

Depending on the surface electric charge, the electroosmotic membranes may be divided in two types, positive electroosmotic membranes and negative electroosmotic membranes. In one embodiment, the positive electroosmotic membrane exhibits a negative zeta-potential under the same buffer/electrolyte conditions that create a positive zeta potential for alumina. For example, the positive electroosmotic membrane may comprise a material with a surface charge similar to silica in DI water and the negative electroosmotic membrane may comprise a material with a surface charge similar to alumina in DI water, and at a neutral pH. In some embodiments, the positive electroosmotic membrane comprises silica, a silicate material, polymeric material or a combination thereof. In some embodiments, positive electroosmotic membrane comprises any porous polymeric material exhibiting a similar zeta potential as silica. In one or more embodiments, the positive electroosmotic membrane comprises polyvinyledene fluoride, polycarbonate, polyester, mixed cellulose ester, nylon or polysulphone. In some embodiments, the negative electroosmotic membrane comprises an alumina material, titania or tantalum pentoxide. Some of the support polymers may be used as EOP membranes, for example, when the polymers are nanoporous and their surface charge is controlled. In one or more embodiments, the membranes may comprise PDMS, COC, PMMA, PC, and combinations thereof.

In one example of the EOP assembly, the AAO is selected as the membrane and cellulose is selected as the electrode, wherein the cellulose for paper) electrodes are coated with a conductive liquid polymer, for example, Pedot:PSS. The AAO membranes are stacked by disposing multiple pieces of paper (cellulose) wetted with a conducting polymer solution as electrodes in between each of the AAO membranes. As noted, the EOP is configured to generate a transverse fluid flow through the AAO and paper stack.

In one embodiment, the electroosmotic membranes used in the EOPs are hydrophilic, which enables the membrane to wet out quickly and completely. The hydrophilic membranes eliminate the need for expensive pre-wetting treatment and increase the flow rate of the fluid passing through the membranes of the EOPs.

In one or more embodiments, the EOPs control the surface zeta potential of the membrane by embedding internal electrodes. For example, by embedding thin Pt electrode layers in the insulating membrane stack, the zeta potential of the surface of the membrane may be actively controlled. The zeta potential of the membrane may vary as a function of buffer, ionic strength and pH, and the surface characteristics. In one embodiment, the electroosmotic membrane has a zeta potential in a range of −100 mV to +100 mV. The magnitude of zeta potential for aluminum oxide in contact with 1 mM KCl, at pH=7 is 37 mV. The zeta potential for silica, zinc oxide, and zirconia is |f|=−80 mV; 45 mV and 90 mV, respectively.

The membranes are stacked to generate a pumping pressure that is proportional to a number of membranes in the pump. Therefore, by increasing the number of membranes, the EOPs are able to increase the operating pumping pressure. As noted, the basic unit structure of the EOP comprises at least two membranes, wherein the surface charges are opposite for two membranes at the time of the fluid flow through the membranes under the influence of the electric field. In some embodiments, the EOP comprises 2 to 100 membranes in series. The total output pressure increases proportionally to the number of membranes within the stack, and the pump is designed based on the application specific fluidic load. The efficiency of the EOPs may be changed, such as increasing or decreasing the pressure, according to the user's need.

FIG. 1 illustrates a simplified unit, structure of battery-free EOP, which comprises at least one porous membrane, wherein the redox polymer electrodes 20, 22 are disposed on both sides of the each of the membranes 12, 16 and wherein one electrode is in oxidized state and the other one is in reduced state. The schematic drawing of the EOP of FIG. 1 further shows that the membrane 12/16 has a nonporous structure comprising a plurality of nanopores 8, wherein the oxidized state of the redox polymer functions as cathode 20 and the reduced state of the redox polymer functions as anode 22. The cathode 20 and anode 22 are operatively coupled by a wired connection 10. In one example of the unit structure of the battery-free EOP, each of the membranes is made of AAO with Pedot:PSS coated on both of the surfaces.

An exemplary low-voltage high-pressure EOP is developed by stacking multiple units of the EOP's to increase a pumping pressure in a portable fluidic system, which is illustrated in FIG. 2. The stacking arrangement of multiple membranes 24, as illustrated in FIG. 2, utilizes alternating nanoporous membranes 12 and 16 with opposing zeta potentials. Each of the membranes is interspersed between two oppositely charged redox polymer based pre-charged electrodes, such as cathode 20 and anode 22. For a stacked EOP, the intervening electrode layers are common, such as for first and second membranes 12 and 16, the intervening electrode is 22, for second and third membranes 16 and 12, the intervening electrode is 20, for third and fourth membranes 12 and 16, the intervening electrode is 22, and so on. The porous membranes and electrodes form channels, such as 28, wherein unidirectional electroosmotic flow is 30. The stacking pattern of the alternating membranes and intervening electrodes enables generation of a unidirectional flow 30 within the applied electric field 26.

The electrodes are operatively coupled to each other, the operative coupling of the electrodes triggers the pump to generate a transverse fluid flow through the membranes. In one or more embodiments, the pump comprises an activation mechanism comprising a manual or automated closure of a conductive path between all electrodes, or selected ones, within the stack. Therefore, the coupling of the selected electrodes leads the activation mechanism for the pump. In one example, the coupling may be automated using an activation switch, in some examples, manual coupling activates the pump. The operative coupling of two or more units of EOP generates a fluid-flow that is proportional to a number of the units of electroosmotic pump coupled in parallel.

Figure 3:
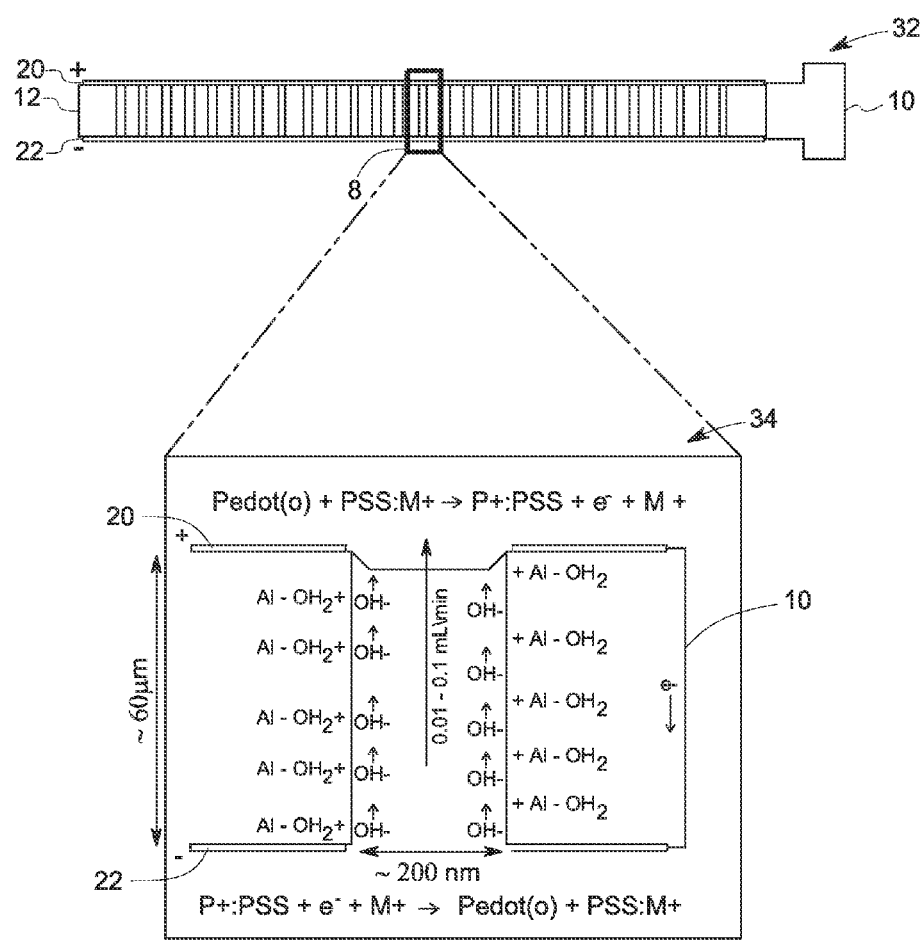
FIG. 3 is an example of a self-contained EOP operation with Pedot:PSS electrodes.

A schematic diagram of an example operation of an EOP assembly using Pedot:PSS saturated cellulose paper electrodes between nanoporous AAO membranes is shown in FIG. 3. The paper electrode has 0.5 mm paper thickness, and the AAO membranes are with 20 nm pore size. FIG. 3 reflects the use of the redox polymer to store charge across the nanoporous EOP material, and thus provide the electric field required to run the EOP. A voltage developed by the redox electrode within the EOP stack results in a passage of an ionic current through the electroosmotic membranes. For example, a voltage developed by the standard Pedot:PSS electrode results in a oxidation-reduction reactions on the electrodes, as shown in FIG. 3. In this case, the current passes across the membranes of the EOP due to the generation of ions by the reactions at the electrodes and the current that exists until reactive sites in the electrodes are exhausted.

Figure 4:
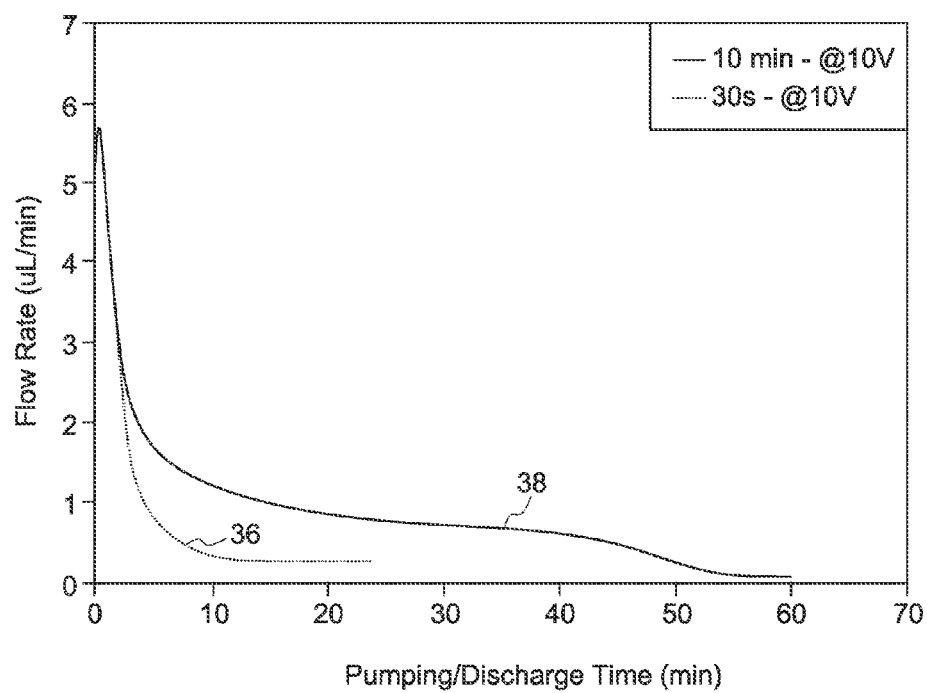
FIG. 4 is an example of a graph showing two different electroosmotic flow profiles after electrode charging at 10V for 10 min or 30 sec.

To maintain a continuous fluid flow through the EOP, a closed circuit and stored chemical potential in the electrodes are used. The discharge of stored chemical potential may be utilized at the time of operating the EOP in a closed circuit, wherein the charged electrode is used as the power source. FIG. 4 is an example of a graph showing two different electroosmotic flow profiles across a 60 nanoporous AAO membrane, wherein the Pedot:PSS electrodes are electrochemically reduced/oxidized, one for 10 min and another for 30 sec at 10 V, resulting in a different amount of charge storage in the self-contained EOP. The redox polymer electrodes are capable of discharging for about 1 hour (38) and for 25 min (36), when the electrodes are electrochemically charged for 10 min and 30 sec respectively. In this embodiment, the EOP is running with a steady flow rate (about 0.5 $\mu L/min/mm^2$) as shown in FIG. 4.

Figure 5:
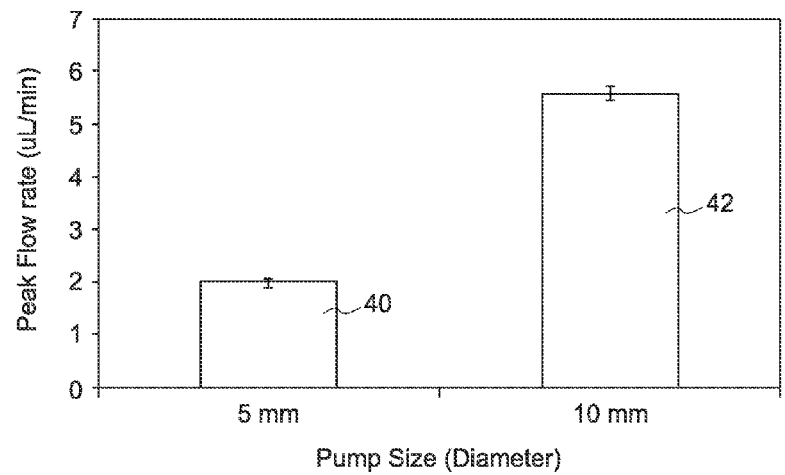
FIG. 5 is an example of a bar graph illustrating flow rates measured from two different self-contained EOPs having different surface area.

The size of the pump mainly depends on the size of the membranes on which the electrodes are typically deposited. The size of an EOP also determines the flow rate of a fluid through the pump. As the fluid passes through the pores of the membranes, therefore a greater number of pores increases the flow rate of the fluid. Therefore, a larger membrane surface area increases the flow rate of the EOP. FIG. 5 illustrates different flow rates from the self-contained EOPs, for differing surface areas. The larger surface area of an EOP contains a larger number of nanopores available for pumping, and thus provides a larger flow rate (42) when compared to an EOP with a smaller surface area (40).

Figure 6:
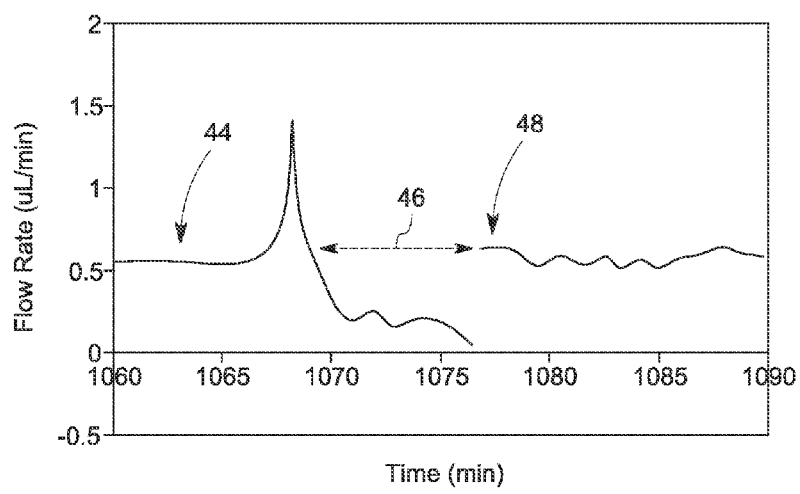
FIG. 6 is an example of a graph showing various phases of self-contained EOP action, including flow rates generated from ionic discharge of the pre-charged electrodes, immediate disruption of the flow upon disconnecting the wire joining the two oppositely charged electrodes, and regaining of the flow rate upon re-connection of the electrodes.

The redox electrodes, for example Pedot:PSS electrodes, of the EOP have the ability to pump liquid, using the stored energy in a charged state when the electric circuit is closed, which results in a steady flow rate, 44 of FIG. 6. Once the circuit is opened, the fluid movement is discontinued through the membrane resulting in a drop in flow rate, 46 of FIG. 6. The flow begins after the circuit is reconnected, as shown in 48, FIG. 6.

The efficiency of the EOPs may be changed, such as, by increasing or decreasing the pressure, or by changing the number of electroosmotic membranes. For example, the stall pressure of an EOP, comprising a double stack of an AAO and silica coated AAO (52), or an EOP comprising a four membrane stack of AAO and silica coated AAO (54) with pre-charged redox electrodes is higher when compared to an EOP with a single AAO with the same electrodes (50), as shown in FIG. 7. The double stack membrane (52) results in a 2× increase in pumping pressure and the four membrane stacks (54) results in a 4× increase in pumping pressure. The flow rates, measured by a commercial micro-electromechanical systems (MEMS) flow sensor, decreases with increasing applied back pressure to the pump and the stall pressure is identified at the zero flow position. In one or more examples, at least two membranes are used to construct a single unit of EOP and this one unit of EOP generates pressure of about 2 PSI. In another example, an EOP constructed with 20 membranes generates a pressure of about 40 PSI.

In the EOPs, the fluid may be electroosmotically pumped through one or more membranes transversely. In one embodiment, the fluid is electroosmotically pumped between two membranes that are stacked one upon another, wherein the membranes are either directly in contact or spaced with a small distance of 1 mm or less. Larger distances within the EOP stack may decrease electric field strengths across the electroosmotic membranes, and therefore flow rates within the pump. Therefore, a pump may sustain high back pressure (e.g., >1 atm) and still maintain adequate fluid flow when a gap between two of the membranes is small, for an example, 500 µm. The EOP of this embodiment increases the pumping pressure associated with low voltage EOPs, enabling use in field-able, self-contained, and battery-operated systems.

In one or more embodiments, the high pressure EOP may comprise a control circuit to maintain a constant current, voltage, fluid flow or pressure output during an operation. In one embodiment, the EOP comprises a controller to maintain a constant fluid flow. In one example, the controller comprises a micro controller circuit. One embodiment of the EOP assembly comprising a controller, as shown in FIG. 8.

Figure 9:
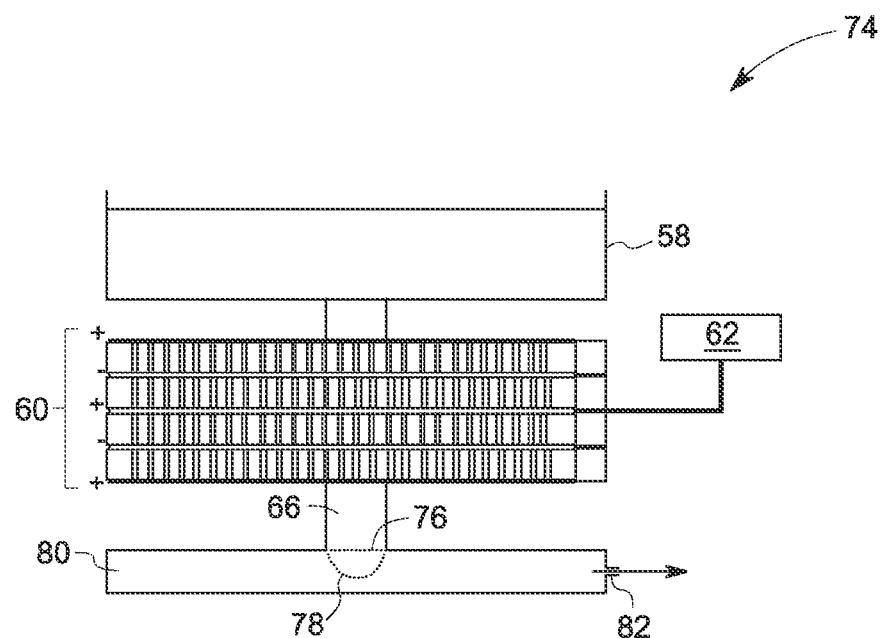
FIG. 9 is a schematic drawing of an example of a method of membrane actuation for pumping fluid using a self-contained unit EOP.
Figure 10:
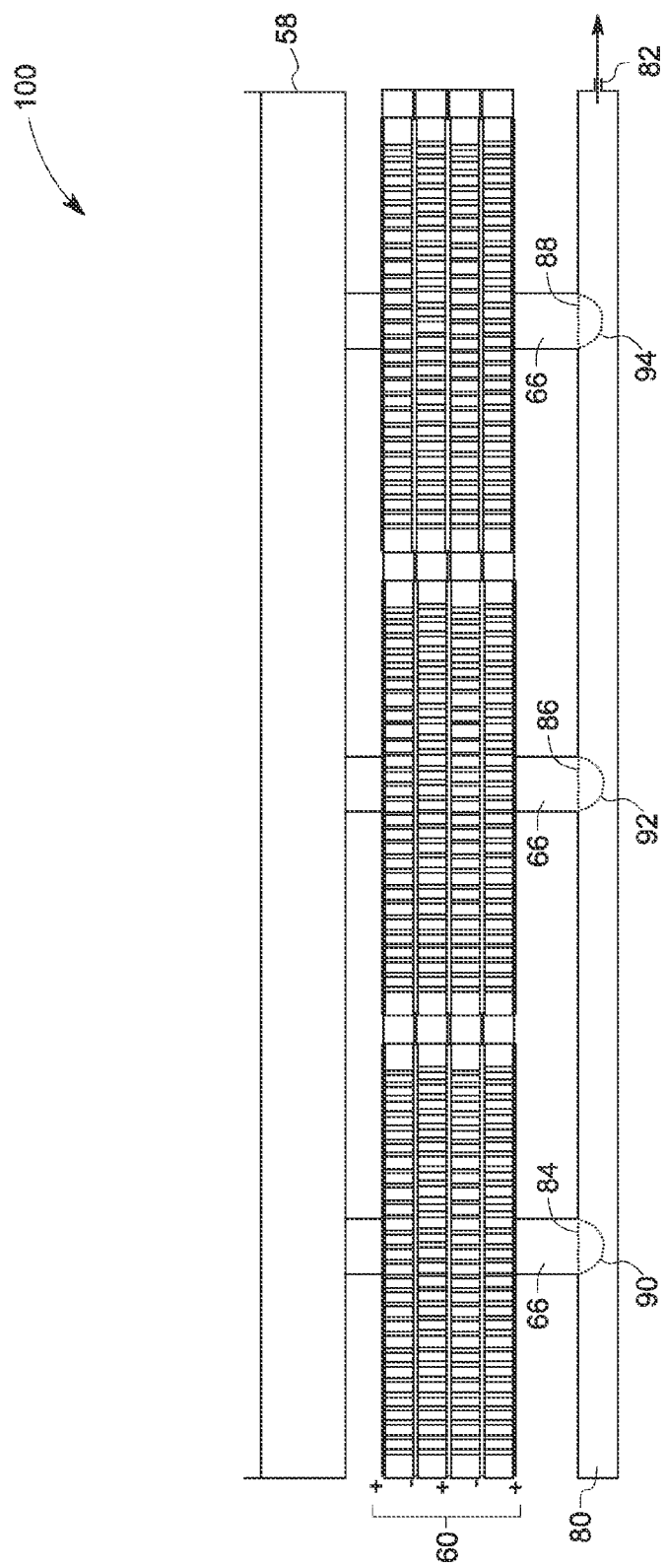
FIG. 10 is a schematic drawing of an example of a method of sequential actuation of membranes for pumping fluid using multiple self-contained unit EOPs.

In some embodiments, the membranes are further operatively connected to at least one fluid reservoir comprising fluid. In some other embodiments, the membranes are operatively connected to two reservoirs comprising fluids. In one example, the EOP assembly is coupled to one or more reservoirs, as shown in FIGS. 8, 9 and 10.

Figure 8:
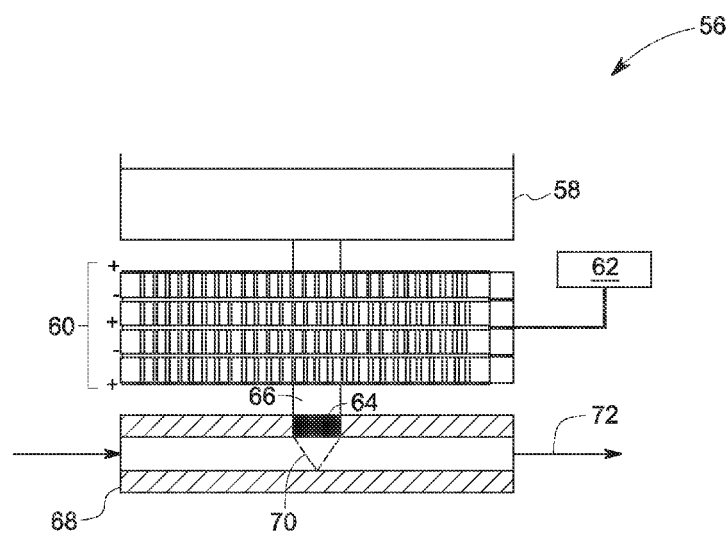
FIG. 8 is a schematic drawing of an example of an assembly of a self-contained unit EOP coupled to a reservoir and a microfluidic channel.

FIG. 8 illustrates an embodiment of an application 56 of the battery free EOP, wherein the EOP (60) is coupled to an upstream reservoir (58) and a downstream microfluidic channel 68. In one embodiment, a controller 62 is coupled to the EOP 60 to control the EOP operation. For example, the controller unit may comprise a microcontroller circuit. As noted, the EOP 60 is coupled to the microfluidic channel 68 by a connector 66 and valve 64. In operation, the fluid from the reservoir may pass through the EOP 60 and generate a pressure, which may actuate the valve 64/70. The actuation of valve prevents the fluid flow through the microfluidic channel 68, as the valve is in open form 70. Alternatively, when the valve is in closed form 64, the fluid 72 flows through the channel 68.

In one embodiment, the pumping liquid or fluid or working solution, which is used in the EOP has a pH from about 3.5 to 8.5. In an alternative embodiment, the pumping solution is a borate buffer with a pH of about 7.4 to 9.2 and an ionic strength between about 25 to about 250 mM.

In one or more embodiments, an EOP may be assembled with one or more reservoirs or chambers comprising fluids, wherein the fluids are different from the working fluid/liquid/solution of the EOP. For example, actuation of a membrane upon application (74) of pressure generated by the battery free EOP is illustrated in FIG. 9, wherein a fluid pumped from a chamber upon membrane deflection. The EOP (60) is coupled to an upstream reservoir (58) and a downstream chamber/reservoir 80. As noted, the EOP 60 is coupled to the chamber 80 by a connector 66 and a membrane 76. In opera on, the fluid from the reservoir may pass through the EOP 60 and generate a pressure, which may actuate the membrane 76 to the deflected form 78. The deflected form of the membrane 78 pushes the previously stored fluid in the chamber 80 to move forward towards the outlet 82. The previously stored fluid in the chamber 80 may be different from the fluid used for EOP operation, which is stored in reservoir 58.

In some other embodiments, multiple EOPs may be assembled with one or more reservoirs or chambers comprising fluids, wherein the fluids are different from the working fluid/liquid/solution of the EOP. For example, sequential actuation of multiple membranes upon application of pressure generated by the battery frees EOPs 100 is illustrated in FIG. 10. The chamber 80 contains a fluid, which flows from the chamber 80 through the outlet 82 upon operation of multiple EOPs, for example, the EOPs 60, 61 and 63 as per FIG. 10. The EOPs are coupled to an upstream reservoir (58) and a downstream chamber/reservoir 80. Each of the EOPs 60, 61 and 63 are connected to the chamber 80 through the membranes 84, 86 and 88 respectively. The fluid pumped from the chamber 80 upon membrane deflection in a sequential manner. In operation of the EOPs, the pressure is generated, which causes the deflection of the membranes and form 90, 92 and 94. The sequential actuation of membranes enables peristaltic pumping of the fluid through the chamber by pushing the stored fluid of the chamber 80 to move forward towards the outlet 82.

Instead of deflection of the membranes 84, 86 and 88, in one embodiment, the membranes 84 and 88 may be deflected to generate over pressure, wherein the membrane 86 may generate under pressure because of EOP operation in backward direction, generating wave like motion for the fluid passes from the chamber 80 to outlet 82. In this embodiment, the membrane 84 pushes the fluid towards the outlet 82, the membrane 86 sucks the fluid in the direction of the reservoir 58 and then membrane 88 again pushes the fluid towards 82.

The core structure for the membrane and electrodes may be adapted to function with other pump components such as, for example, fluid chambers, inlet port(s), and outlet port (s). Moreover, high pressure EOPs may be coupled to one or more mechanical valves and switches, and used as an actuating pressure source, in contrast to a conventional fluid pump. Furthermore, implementation of such self-contained fluid control systems from a limited number of materials using simple fabrication techniques enable application of the portable pump and control elements within the disposable cartridges. Some more examples include, electroosmotic valves using the EOPs by opposing pressure driven flow, use of the EOPs to fill and empty flexible reservoirs to induce functionality via shape change and electroosmotic-actuators. A benefit for at least one of the embodiments is high throughput screening and compound profiling.

In one embodiment, the EOP is packaged with one or more pre-charged or chargeable or rechargeable electrodes to make the entire pump assembly be self-contained. The low voltage operation requires minimal current draw within each of the serially connected membranes of the EOPs. The multiple membrane-based EOPs generate higher pressures without a power supply.

The EOPs may also be integrated within micro-meter and millimeter scale fluidic systems by, for example, stacking them together to increase the pressure output or to maintain flow rate to overcome the viscous losses and pressure loads in long channels. The devices may be run on an electrode charge and can thus enable a variety of hand held devices.

An EOP assembly may be disposed in a channel to form an electroosmotic flow setup. The channel may be a microfluidic channel. In some examples, gas bubbles are released on the Pt electrode surface and impede flow through the EOP. However, in one embodiment of the multiple membrane-based EOP, stable flow rates of the fluid may be achieved within seconds, even when pumping into channels or structures with high hydraulic resistance. This is due to the high pumping pressure of the stacked EOPs and the fact that, the redox electrodes reduce bubble formation within the pump and therefore allow use of the EOPs in microchannels without interruption.

A method of making an electroosmotic pump, comprises disposing a plurality of membranes comprising one or more positive electroosmotic membranes and one or more negative electroosmotic membranes in an alternative fashion to form a membrane stack; disposing a plurality of electrodes comprising cathodes and anodes, wherein the electrodes are pre-charged, chargeable, rechargeable or combination thereof and wherein at least one of the cathodes is disposed on one side of one of the positive electroosmotic membrane or negative electroosmotic membranes and at least one of the anodes is disposed on another side of that membrane, and at east one of the cathodes or anodes is disposed between a positive electroosmotic membrane and negative electroosmotic membrane. The electrodes are operatively coupled to complete a circuit for activating the electrodes to generate a chemical potential across the membranes.

While snaking a redox polymer electrode, in one or more examples, a piece of porous membrane is soaked in a redox-polymer to form a redox-polymeric coating on the nanoporous membrane, wherein the redox-polymeric coating is used as an electrode layer on the membrane surface. For example, a cellulose membrane is soaked in the redox polymer Pedot:PSS and used as electrode. In one specific example, a piece of alumina oxide (Anodisc®) membrane is encased in a redox polymer Pedot:PSS. The redox polymer is oxidized on one side of the membrane and reduced on the other; generating a chemical potential across the nanopores. For example, the Pedot is oxidized on one side of the membrane and is reduced on the other side, developing a chemical potential across the nanopores of the membrane.

In some embodiments, while making an EOP, the membranes are coated with polymeric material using various methods. In some embodiments, the AAO membrane is coated using a sol-gel material deposition, chemical vapor deposition (CVD) atomic layer deposition (ALD), or molecular vapor deposition (MLD). The fabrication techniques are used to produce the AAO membrane with an expected surface charge. For example, a bare AAO membrane contains a positive surface charge in water. In another example, the bare AAO membrane, is treated with silica to form the silica coated membrane that contains the negative surface charge in water. By selecting an appropriate surface coating material such as silica, the flow rate of the fluid passing through the membrane may be increased.

The battery-free EOP replaces the expensive platinum with conductive polymers as electrode material and led to the discovery that pre-charged redox polymers are used as batteries to power the pump. Embodiments of the battery-free EOP enable to develop a low-cost, disposable pump with an integrated power source, for use in point-of-care diagnostic devices. The applications for EOPs include, but are not limited to, lab-on-a-chip devices and applications, inkjet printing, ink delivery, drug delivery, liquid drug delivery, chemical analysis, chemical synthesis, proteomics, healthcare related applications, defense and public safety applications; medical applications, pharmaceutical or biotech research applications, environmental monitoring, in vitro diagnostic and point-of-care applications, or medical devices. In one embodiment, the EOPs may also be incorporated into MEMS devices. Other applications include, but are not limited to, PCR (DNA amplification, including real time PCR on a chip), electronic cooling (e.g. for microelectronics), pumping ionized fluids and colloidal particles, or adaptive microfluidic mirror arrays.

Example 1

Fabrication of EOPs

Materials: The Anodisc® membranes (GE Healthcare), are available in a package of 100 membranes. The silica membranes were made by coating GE's Anodisc® membrane with $SiO_2$ using either treatment in a sol-gel solution or deposition within an atomic layer deposition chamber. Silica sol gel was produced using raw materials from Sigma Aldrich, including TEOS (Tetraethyl orthosilicate), CAT#86578-250 ml. ALL) coating was performed using tris(tert-butoxy)silanol and tri-methyl-aluminum as the precursors. Pedot:PSS electrodes were fabricated in-house using a solution purchased from Sigma-Aldrich, (St. Louis, Mo.). The Anodisc® membranes are used as bare Anodisc® and also after the silica treatment. Alternatively, in one example, nanoporous PVDF membranes were used in place of silica treated Anodisc® membranes, as the material share similar zeta potential. The cellulose or paper sheets were acquired from Whatman™. A Keithley 2400 SourceMeter commercial power source and a disposable paper battery from Power Paper Ltd. (Petach Tikva, Israel) were used as power sources.

EOP was assembled by using an electrode made of cellulose or paper, whereby large cellulose sheets (Whatman™) were stretched within a metal frame, and saturated with a conductive polymer PEDOT:PSS, followed by drying. Alternatively, the electroosmotic membranes may be directly spin coated with PEDOT:PSS solution, followed by drying and etching. In other embodiments, a porous metal mesh was dip coated by PEDOT:PSS solution and dried. After a solvent treatment to render the PEDOT:PSS conductive and a brief drying period, electrodes were cut from the large sheet via laser machining or physical punching, and the paper electrodes were disposed between the alternating nanoporous ceramic membranes, as shown in FIG. 2. By this method, the metallization of the Anodisc® which was used in other examples for making the EOPs, was replaced, and the paper electrodes were stacked using automated pick-and-place equipment. In addition, each Anodisc® was cushioned between the cellulose electrode layers, providing a physical robustness to the EOP stack. This alternative arrangement of membranes and electrodes was laminated to form EOPs within plastic cartridges without damage to the fragile, internal ceramic membrane structure. A small 8 mm diameter EOP assembly was used. Each unit structure of EOP was primed with DI water, mounted to a MEMS flow sensor, and a DC voltage was applied across each electroosmotic membrane using the paper electrodes within the stack.

After assembling of the EOPs, the integrated EOP was loaded into a plastic housing and primed with a fluid, such as DI water or borate buffer. A copper wire was used to connect the two oppositely charged electrodes. Then the wire terminals are attached to the two electrodes in the membrane stack/EOP. An exact voltage was derived from the redox electrodes, which was applied to the EOP. A MEMS flow sensor was placed in a series with the EOP, and flow rates were measured at the membrane stack exit. A back-pressure (from the fluid column) was then applied to examine the maximum pumping pressure of the stack (the pressure at which the pump stalls is considered the maximum pressure output from the EOP).

The flow rate of the EOP was monitored to check the pump efficiency. A brief burst at flow onset is due to the primed liquid exiting the capillary containing the MEMS sensor, however it quickly reaches a stable flow rate within seconds.

Example 2

EOP Operation Using Various Electrode Materials

The EOPs work by passing ions at the surface of the electrodes, through opposite ends of the nanopores of the membranes wherein, the electrons flow from oxidized to reduced electrodes as described in FIG. 3. In this example, the conductive or redox polymer PEDOT/PSS was used as the electrode. The PEDOT/PSS electrode has the advantages of minimizing bubble formation without large over potentials due to hydrolysis. In addition, internal redox within the conductive polymer (PEDOT/PSS) coated paper electrodes provided an internal driving mechanism to drive ions and generate the current necessary to run the EOP, as shown in FIG. 3. The voltage, which was applied on the PEDOT/PSS electrode, resulted in a redox reaction within the bulk of the material, thus use of the high capacity cellulose as the electrode support substrate enabled increased coulombic capacity for driving the pump over longer periods of time.

Example 3

Charge Storage Capacity of Redox Polymer Electrodes

The experiment was performed to determine the storage capacity of the redox polymer electrodes, by using Pedot:PSS electrodes in an EOP. The membranes were circular in shape and the area of the cellulose membranes was about 20 mm$^2$. The cellulose membranes were soaked in Pedot:PSS polymer solution. Due to the capacity of the cellulose (paper) membrane to retain liquid, the charge storage of a cellulose membrane might be more compared to other type of membranes. In one example, the electrodes were charged for about 10 min at about 10 V before using the electrodes in the EOP (38) and in another example, the electrodes were charged for about 30 sec at 10 V (36) as shown in FIG. 4. In the first example, the potential was generated of about 1 V and the flow 38 continued for about 1 hour with a constant flow rate of about 0.5 μL/min (FIG. 4). In the second example, the flow 36 continued for only 25 min, while the electrodes were charged for 30 sec.

Therefore, the quantity of stored charge is one of the factors that determine the length of time for continuous flow in an EOP. The magnitude of charge of the electrode may be altered to change the flow rate, or the electrical resistance of the wire may be altered in order to change the discharge or flow time. The flow magnitude may be increased by storing more charge in the electrodes or by increasing the surface area of the membranes.

Example 4

Determination of Pumping Efficiency Using EOPs with Membranes Having Different Surface Area In this example, the electrodes were electrochemically reduced/oxidized which enabled separation of charge stored within the Pedot across the nanoporous EOP membranes. The flow rates were measured from two different self-contained EOPs with membranes having different surface area. Pedot:PSS electrodes were electrochemically reduced/oxidized for 10 min at 10 V. Two different AAO membranes were selected for the two EOPs, wherein one of the membranes had a 5 mm diameter and the another had a 10 mm diameter, resulting in different flow rates through the self-contained EOPs. FIG. 5 shows the bar graphs for flow rates from the different EOPs with membranes of different surface areas. The larger surface area pump contains a larger number of nanopores available for pumping, and thus provides a larger flow rate 42, when compared to the flow rate from the smaller surface area pump 40. The AAO membrane/Pedot:PSS electrode established an average flow rate of 0.09 (μL/min) per mm$^2$ of pump surface area.

Example 5

Determination of Pumping Ability of an EOP Stack Using Stored Energy in the Redox Polymer Electrode The example demonstrates the ability of an EOP to pump liquid, using the stored energy in the redox polymer electrodes, in a charged state when the electric circuit was closed. Once the circuit was opened, the fluid movement was discontinued through the membrane. The flow began after the circuit was reconnected. The reconnection results in discharge of the chemical potential energy that was stored in the redox polymer electrodes as shown in FIG. 6.

The graph of FIG. 6 illustrates the change in flow rate of the fluid with time for an EOP driven by the discharge of the chemical potential stored in the redox electrodes. The graph shows a continuous flow 44 with a flow rate of ~0.5 μL/min before disconnection of the wire, after disconnection of the wire the flow rate 46 was abruptly dropped to ~0 μL/min, and after reconnection of the wire, the flow rate 48 again reached to ~0.5 μL/min. Therefore, the wired-connection of two oppositely charged electrodes results fluid flow through the EOP due to the discharge of the stored chemical potential in the redox polymer electrodes, which was discontinued during disconnect of the electrodes and further continued on reconnection.

Example 6

Determination of Stall Pressure by Increasing Number of Membranes

Results were generated measuring the stall pressure of an EOP comprising Anodisc® as membranes and Pedot:PSS as electrodes. A unit EOP, two units of stacked EOP, and four units of stacked EOP were used for this example, wherein the EOPs are low-voltage, high pressure EOPs. The pumping pressures may be tuned to application-specific values based on the intelligent assembly scheme, as shown in FIG. 2. The flow rates were measured using a commercial MEMS flow sensor, Sensirion CMOSENS LG16-1000D, after the increased pressure load was applied to the pump. The pumping pressure may be increased or decreased according to the pressure requirement for specific applications by increasing or decreasing the number of membranes in the EOP. Flow rates were measured using a commercial MEMS flow sensor as increased back pressure was applied to the pump. FIG. 7 shows increased pumping pressure realized by an embodiment of an EOP with multiple porous substrates, wherein each membrane was sandwiched by pre-charge electrodes of opposite charges. There was a 2× increase in pumping pressure within the double units of stacked EOPs (52) and 4× increase in pumping pressure within the four units of stacked EOPs (54), when compared to a single unit of EOP (50), as shown in FIG. 7. Therefore, two or more units of EOPs, which are operatively coupled, generated a fluid-flow that is proportional to a number of the units of EOP coupled in parallel.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A pump, comprising:
a plurality of electroosmotic membranes comprising one or more positive electroosmotic membranes and one or more negative electroosmotic membranes; and
a plurality of conductive polymer electrodes comprising one or more cathodes and one or more anodes;
wherein the electrodes are store a chemical potential across the electroosmotic membranes sufficient to operate the pump in the absence of any externally applied electrical potential;

wherein the positive electroosmotic membranes and negative electroosmotic membranes are disposed alternately to form a membrane stack;

wherein at least one cathode is disposed on one side of one of the membranes and at least one anode is disposed on another side of that membrane and the at least one cathode and the at least one anode are operatively coupled to each other, and wherein at least one cathode or anode is disposed between a positive electroosmotic membrane and a negative electroosmotic membrane.

2. The pump of claim 1, configured to generate a pressure of at least 0.75 PSI.

3. The pump of claim 1, wherein the electrodes comprise a material capable of generating a chemical potential up to 3 V across the membranes.

4. The pump of claim 1, wherein the electrodes comprise a material capable of discharging for about 1 hour while running the pump with a flow rate between 0 and 5 μL/(min*mm$^2$).

5. The pump of claim 1, wherein the electrodes are rechargeable for 1 to 5000 times.

6. The pump of claim 1, wherein the electrodes comprise charges in a state that is dry, semi-dry or wet state.

7. The pump of claim 1, wherein the electrodes comprise one of a oxidation-reduction polymer material, metal oxide, graphene, carbon nanotubes or combinations thereof.

8. The pump of claim 1, wherein the electrodes comprise one of a poly(3,4-ethylenedioxythiophene):polystyrenesulfonate (Pedot-PSS), Pedot-(molybdenum trioxide), poly(3-(4-fluorophenyl)thiophene) (MPFT), poly(3-(4-fluorophenyl)-thiophene) (PFPT), poly(3-methyl thiophene) (PMeT) or poly(l-cyano-2-(2-(3,4-ethylenedioxylthienyl))-1-(2-thienyl)vinylene (ThCNVEDT), PDTT polymer or combinations thereof.

9. The pump of claim 1, further comprising a micro controller circuit to maintain a constant current, voltage, fluid flow, pressure output or combinations thereof.

10. The pump of claim 1, wherein the membranes are configured to generate an electroosmotic flow of about 0.05 to 5 μL/(min*mm$^2$).

11. The pump of claim 1, wherein the membranes comprise nanopores having a diameter between 10 to 500 nm.

12. The pump of claim 1, wherein the membranes are configured to operate the pump by applying an electric field of at least 100V/m across each of the membranes.

13. The pump of claim 1, wherein the membranes have a thickness between 10 nm to 10 mm.

14. The pump of claim 1, comprising 2 to 100 membranes.

15. The pump of claim 1, wherein the membranes comprise one of a tungsten oxide, a vanadium oxide, a silicon dioxide, a silicate, a silicon carbide, a tantalum oxide, a hafnium oxide, a tin oxide, a manganese oxide, a titanium oxide, a silicon nitride, a chromium oxide, an aluminum oxide, a zinc oxide, nickel oxide, a magnesium oxide or combinations thereof.

16. The pump of claim 1, wherein the positive electroosmotic membrane comprises a silica, a silicate material, polymeric material or a combination thereof.

17. The pump of claim 1, wherein the positive electroosmotic membrane comprises one of polyvinyledene fluoride, polycarbonate, polyester, mixed cellulose ester, nylon, polysulphone or combinations thereof.

18. The pump of claim 1, wherein the negative electroosmotic membrane comprises an alumina material, titania or tantalum pentoxide.

19. The pump of claim 1, wherein the operative coupling of the electrodes is a trigger mechanism for a transverse fluid flow through the membranes.

20. The pump of claim 19, wherein the fluid-flow is proportional to a number of units of electroosmotic pump coupled in parallel, wherein each unit electroosmotic pump comprises one positive electroosmotic membrane and one negative electroosmotic membrane, and at least one cathode and one anode.

21. The pump of claim 1, wherein the membranes are stacked to generate a pumping pressure that is proportional to a number of membranes in the pump.

22. The pump of claim 1, comprising a stack of two or more unit electroosmotic pumps, wherein each unit electroosmotic pump comprises one positive electroosmotic membrane and one negative electroosmotic membrane, and at least one cathode and one anode, wherein the two or more unit electroosmotic pumps are operatively coupled in parallel.

23. The pump of claim 1, wherein the membranes are operatively connected to at least one fluid reservoir.

24. The pump of claim 1, wherein the pump comprises an activation mechanism comprising a manual or automated closure of a conductive path between all electrodes, or selected ones, within the stack.

25. The pump of claim 1, wherein the electroosmotic membranes are operatively coupled to one of a mechanical valve, a membrane, a diaphragm or combination thereof.

26. The pump of claim 1 is further operatively coupled to a separate reservoir, chamber, or channel via a flexible membrane for pumping a fluid from the reservoir, chamber, or channel by actuation of the membrane.

27. A pump, comprising:
a plurality of electroosmotic membranes comprising one or more positive electroosmotic membranes and one or more negative electroosmotic membranes, wherein each of the positive electroosmotic membranes and negative electroosmotic membranes are disposed alternately;
a plurality of conductive polymer electrodes comprising one or more cathodes and one or more anodes, wherein the electrodes store a chemical potential across the electroosmotic membranes sufficient to operate the pump in the absence of any externally applied electrical potential, and the cathode and anode are operatively coupled to each other,
wherein at least one cathode is disposed on one side of one of the membranes and at least one anode is disposed on another side of that membrane,
wherein at least one of the cathodes or anodes is disposed between a positive electroosmotic membrane and negative electroosmotic membrane, and
wherein the electrodes are operatively coupled to generate and store a voltage of up to 3 V volts to generate a pressure of at least 0.75 PSI.

* * * * *